United States Patent [19]

Christensen et al.

[11] 4,152,529

[45] May 1, 1979

[54] DEALKYLATION OF HALOGENATED ALKYL SUBSTITUTED PHENOLS

[75] Inventors: Nils J. Christensen, Palatine; Joseph Levy, Northbrook, both of Ill.

[73] Assignee: UOP Inc., Des Plaines, Ill.

[21] Appl. No.: 851,901

[22] Filed: Nov. 16, 1977

[51] Int. Cl.$^2$ .............................................. C07C 39/24
[52] U.S. Cl. ..................................... 568/775; 568/805
[58] Field of Search ....................... 260/623 R, 621 D; 568/788, 790, 780, 775, 805

[56] References Cited

U.S. PATENT DOCUMENTS

| | | | |
|---|---|---|---|
| 2,603,662 | 7/1952 | Stevens | 260/624 R |
| 2,802,884 | 8/1957 | D'Alelio | 568/780 |
| 2,950,325 | 8/1960 | Britton et al. | 260/623 R |
| 3,461,175 | 8/1969 | Kulik et al. | 568/788 |
| 3,534,111 | 10/1970 | Hess | 568/788 |
| 3,933,927 | 1/1976 | Goddard | 568/780 |

*Primary Examiner*—Werren B. Lone
*Attorney, Agent, or Firm*—James R. Hoatson, Jr.; Raymond H. Nelson; William H. Page, II

[57] ABSTRACT

Halogenated alkyl substituted phenols may be dealkylated by treating a compound such as 5-t-butyl-2-fluorophenol with a diealkylation catalyst such as an acid acting compound at dealkylation conditions whereby the t-butyl substituent is removed and the resulting compound comprising 2-fluorophenol is recovered.

7 Claims, No Drawings

DEALKYLATION OF HALOGENATED ALKYL SUBSTITUTED PHENOLS

BACKGROUND OF THE INVENTION

With the advent of aircraft which are able to fly at relatively high speeds greater than Mach 1 plus the ability to climb to high altitudes, it is necessary to provide an oxygen system which will perform under these relatively harsh conditions. This is especially true in the case of military aircraft which must possess the ability to fly higher, faster, longer and with greater maneuverability than other aircraft. In supplying an oxygen system for the cockpit of military aircraft, it is necessary to have a system which will perform in an adequate manner and which will be relatively light in weight. Another criteria is that the system be relatively small in size inasmuch as the cockpit area, especially in pursuit or fighter aircraft, is relatively small. One method of supplying oxygen to the personnel on the aircraft is to store oxygen as a liquid. One advantage in using such a system is that liquid oxygen does not require a high pressure tank and the ratio of system volume and weight versus the usable material could be drastically reduced. However, the disadvantage to the use of such a system is that expensive equipment is required on the ground in order to handle the problems of handling the cryogenic liquid.

As an alternative to using the relatively expensive liquid oxygen system, it has been found possible to concentrate oxygen use of the air and provide it to the aircraft crew members via certain metal chelates. One such metal chelate which has been found to be effective in the generation of oxygen from air is cobalt bis(3-fluorosalicylaldehyde)ethylenediimine which is known as fluomine. This cobalt chelate compound can reversibly bind oxygen and generate it by absorbing the oxygen at low temperatures and desorbing it at higher temperatures. For example, fluomine will absorb oxygen at a maximum rate between 80° and 100° F. while the desorption of the oxygen will take place above about 180° F. at relatively low pressures. A precursor to the aforementioned fluomine comprises 3-fluorosalicylaldehyde. This compound is prepared in a series of steps utilizing o-fluorophenol as the starting material.

Heretofore, the commercial source of o-fluorophenol was as a byproduct resulting from the production of p-fluorophenol. The production of the isomeric fluorophenols resulted from p-nitrochlorobenzene which was contaminated with o-nitrochlorobenzene and the yield of the isomeric fluorophenols from the isomeric nitrochlorobenzenes usually ranged from 45% to 80%. Other direct ways of obtaining the desired product starting with o-nitrochlorobenzene are multi-step and elaborate in nature utilizing such compounds as potassium fluoride and dimethylsulfoxide as well as nitric acid and sulfuric acid. By utilizing these compounds it is necessary to use relatively expensive and elaborate equipment and therefore, it is not economically feasible to obtain the desired product by utilizing these methods. As will hereinafter be set forth in greater detail, we have now discovered that it is possible to obtain a halogenated phenol such as o-fluorophenol by dealkylating a halogenated alkyl substituted phenol in a relatively simple manner.

This invention relates to a process for the dealkylation of a halogenated alkyl substituted phenol. More specifically, the invention is concerned with a process for dealkylating alkyl substituted fluorophenols. As hereinbefore set forth, halogenated phenols such as o-fluorophenol may be utilized as starting materials in preparing compounds which are useful for generating oxygen. In order to obtain a process whereby the desired chelate is prepared in an economical manner, it is necessary that all steps that are required for the production of the product be operated in like manner. Inasmuch as the starting material for preparing cobalt bis(3-fluorosalicylaldehyde)ethylenediimine is o-fluorophenol, it is necessary that this starting material costs as little as possible. The steps of synthesizing this starting material are relatively complex inasmuch as fluorobenzene must be subjected to a series of condensations and dealkylations in order to obtain the desired product.

It is therefore an object of this invention to provide an improved process for the dealkylation of halogenated alkyl substituted phenols.

A further object of this invention is to provide an improved process for the dealkylation of halogenated alkyl substituted phenols whereby the desired product comprising a halogenated phenol will be obtained in improved yields.

In one aspect an embodiment of this invention resides in a process for the dealkylation of a halogenated alkyl substituted phenol which comprises treating said phenol at dealkylation conditions in the presence of an acid acting catalyst, and recovering the resulted halogenated phenol.

A specific embodiment of this invention is found in a process for the dealkylation of a halogenated alkyl substituted phenol which comprises treating 5-t-butyl-2-fluorophenol at a temperature in the range of from about ambient to about 300° C. and a pressure in the range of from about atmospheric to about 100 atmospheres in the presence of an acid acting catalyst comprising an aluminum chloride and an acceptor compound for the eliminated alkyl moiety comprising toluene, and recovering the resulting 2-fluorophenol.

Other objects and embodiments will be found in the following detailed description of the present invention.

As hereinbefore set forth the present invention is concerned with a process for the dealkylation of halogenated alkyl substituted phenols. The starting materials which comprise these compounds may be obtained from any source known in the art. For example, one method of approach for obtaining the starting materials may comprise alkylating a fluorobenzene with an olefin or an alkyl halide as the alkylating agent to introduce a bulky alkyl group, comprising a tertiary or secondary alkyl group, of which the tertiary alkyl group is preferred, in the para position. The alkylation of the fluorobenzene is preferably effected at temperatures ranging from about 0° up to about 50° C. or more in the presence of a conventional alkylation catalyst. Examples of alkylating agents which may be employed to form the desired product will preferably include olefins or alkyl halides containing from about 4 to 10 carbon atoms such as isobutylene, isopentene, isohexene, isoheptene, isooctene, isononene, t-butylchloride, t-butylbromide, 2-chloro-2-methylbutane, 2-bromo-2-methylbutane, 2-chloro-2-methylpentane, 2-bromo-2-methylpentane, 3-bromo-3-methylpentane, 2-chloro-2-methylhexane, 3-bromo-3-methylhexane, 3-chloro-3-methylheptane, 4-bromo-4-methylheptane, etc.

The thus formed para-alkylfluorobenzene may then be brominated at temperatures ranging from about 0° to about 75° C. in the presence of a catalyst such as iodine, iron, etc., to form a 4-alkyl-2-bromofluorobenzene. The latter compound may then undergo hydrolysis by treating the compound with water in the presence of catalysts such as potassium fluoride and cuprous oxide at elevated temperatures ranging from about 200° to about 300° C. under pressures ranging from about 1 to 100 atmospheres. The hydrolysis will result in the preparation of 5-alkyl-2-fluorophenols.

The aforementioned 5-alkyl-2-fluorophenols may then be subjected to dealkylation by treating the compounds with a dealkylation catalyst comprising an acid acting compound at dealkylation conditions which will include a temperature in the range of from about ambient (20°-25° C.) up to about 300° C. or more and at pressures ranging from atmospheric to about 100 atmospheres. In the event that elevated temperatures within the upper limit of the range hereinbefore set forth are employed and super-atmospheric pressures are utilized, the latter may be afforded by the introduction of a substantially inert gas such as nitrogen, argon, helium, etc., into the reaction zone, the amount of pressure which is employed being that which is sufficient to maintain a major portion of the reactant in the liquid form. Examples of acid acting catalysts which may be employed to effect dealkylation will include such compounds such as Friedel-Crafts metal halides including aluminum chloride, ferric chloride, zinc chloride, stannic chloride, etc., protonic acids such as polyphosphoric acid, orthophosphoric acid, Solid Phosphoric Acid, p-toluenesulfonic acid, benzenesulfonic acid, acid clays such as acidic silicates, and acidic metal oxides such as alumina, silica-alumina, etc. In the preferred embodiment of the invention, in addition to the acid acting catalyst, the reaction zone will also contain an acceptor compound for the eliminated alkyl moiety, which may be transferred to the acceptor compound as a carbonium ion complex with the acid catalyst. The acceptor compound will preferably consist of an active aromatic compound containing substituents not readily eliminated or isomerized by the acid catalyst such as toluene, xylene, etc.

The process of the invention may be effected in any suitable manner and may comprise either a batch or continuous type of operation. For example, when a batch type operation is employed a quantity of the halogenated alkyl substituted phenol which may be prepared according to the description hereinbefore set forth and the acid acting catalyst, the latter being present in a molar excess in the range of from about 1.1:1 up to about 1.5:1 moles of catalyst per mole of phenol, are placed in an appropriate apparatus. The acid acting catalyst is present in slightly excessive amount in order that a portion of the catalyst remains uncomplexed with the phenolic group in order to effect the dealkylation of the phenol. In addition, if so desired, an acceptor compound such as toluene as hereinbefore described, is also present in the reaction vessel. Following the addition of the reactant catalyst and acceptor compound, the apparatus and contents thereof are then heated to the desired temperature within the range hereinbefore set forth and continuously agitated during the dealkylation time which may range from about 0.5 up to about 30 hours or more in duration. At the end of this period of time the apparatus and contents thereof are allowed to return to room temperature and the reaction mixture subjected to conventional means of separation whereby the desired halogenated phenol is separated from any unreacted starting materials, olefin, catalyst and the alkylated acceptor compound by-product.

It is also contemplated within the scope of this invention that the process for the dealkylation of the halogenated alkyl substituted phenol may be accomplished in a continuous manner of operation. When such a type of operation is used the halogenated alkyl substituted phenol is continuously charged to a reaction vessel which is maintained at the proper operating conditions of temperature and pressure. In addition the reaction vessel will also contain an acid acting catalyst of the type hereinbefore set forth in greater detail. If so desired the acceptor compound such as toluene may also be charged to the reactor through a separate line or, if so desired, it may be admixed with the halogenated alkyl substituted phenol prior to entry into said reactor and the resulting admixture charged thereto in a single stream. In the event that the acid acting catalyst is in solid form the dealkylation may be effected using a fixed bed method in which the catalyst is disposed in the reactor as a fixed bed and the halogenated alkyl substituted phenol is passed through said bed in either an upward or downward flow. Other conventional types of continuous operating procedures may also be employed. When employing such continuous processes for effecting the dealkylation, the reactor effluent is continuously withdrawn from the reaction zone after passage of the desired reaction time and subjected to conventional means of separation whereby the desired halophenol is separated and recovered while any unreacted starting material, catalyst, and alkylated acceptor by-product compound are also recovered and the unreacted starting material, in particular, recycled to the reaction zone to form a portion of the feedstock.

Some examples of halogenated tertiary or secondary alkyl substituted phenols which may undergo dealkylation to form the corresponding ortho-halophenol will include 5-t-butyl-2-bromophenol, 5-t-butyl-2-fluorophenol, 5-t-butyl-2-iodophenol, 5-sec-pentyl-2-bromophenol, 5-sec-pentyl-2-fluorophenol, 5-sec-pentyl-2-iodophenol, 5-sec-hexyl-2-bromophenol, 5-sec-hexyl-2-fluorophenol, 5-sec-hexyl-2-iodophenol, 5-sec-heptyl-2-bromophenol, 5-sec-heptyl-2-fluorophenol, 5-sec-heptyl-2-iodophenol, etc. It is to be understood that the aforementioned halogenated alkyl substituted phenols and corresponding halophenols are only representative of the class of compounds which may be used in the present process, and that the process of the present invention is not necessarily limited thereto.

The following examples are given for purposes of illustrating the process of the present invention. However, it is to be understood that these examples are given merely for purposes of illustration and that said invention is not necessarily limited thereto.

EXAMPLE I

In this example 5-t-butyl-2-fluorophenol, the starting material for the dealkylation process of this invention, was prepared by first alkylating 480 grams of fluorobenzene with 370 grams of t-butylchloride in the presence of 16.6 grams of aluminum chloride and 33 grams of nitromethane as solvent for the reaction at a temperature ranging from about 0° to 2° C., the t-butylchloride being added incrementally to the mixture of fluorobenzene, aluminum chloride and nitromethane in about 2.5 hours and maintained for about an additional hour at this temperature. The resulting 4-t-butyl-fluorobenzene was recovered by treating the reaction mixture with 150 ml water at 0°–10° C. followed by washing with 5% aqueous NaOH, and the organic layer was then separated, followed by fractionation at about 5 mm reduced pressure and 547 grams of product collected from about 48°–52° C. to yield about a 70% conversion and 86% selectivity to p-t-butylfluorobenzene via gas liquid chromatographic analysis. Following this 304 grams of 4-t-butylfluorobenzene so prepared and a catalyst comprising 12.3 grams of iodine were placed in another reaction apparatus and brominated by incrementally adding about 372 grams of bromine during a period of about 3 hours while maintaining the temperature of the reaction at about 60°–65° C., and then maintaining the reaction mixture for about an additional 9 hours. Upon completion of the bromination the organic layer was washed with saturated sodium thiosulfate solution and then with water, dried and the recovered 312 grams of product was fractionated under a reduced pressure of about 3 mm to isolate about 224 grams of the desired 4-t-butyl-2-bromofluorobenzene distilling at about 40°–77° C. The heart cut of this distillate of about 171 grams analyzed about 90% pure via gas liquid chromatography. To obtain the next product comprising 5-t-butyl-2-fluorophenol the thus formed 4-t-butyl-2-bromo-fluorobenzene (20.0 grams) was hydrolyzed by treatment with 160 ml of water in the presence of 18.6 grams of potassium fluoride and 1.0 grams of cuprous oxide plus 40 grams of sulfolane as a co-solvent, said reaction being effected at an elevated temperature of 250° C. and under a nitrogen atmosphere at a total pressure of about 525 pounds per square inch. At the end of about eight hours of reaction period, the autoclave and contents thereof were allowed to return to room temperature, the excess pressure was discharged, and the product recovered from the mixture by extraction with toluene. Distillation under reduced pressure provided about 11.4 grams of the desired product comprising 5-t-butyl-2-fluorophenol corresponding to a conversion of about 85% and a selectivity of about 70%. N-methyl-pyrrolidone may also be effectively used as the co-solvent in this hydrolysis.

5-T-butyl-2-fluorophenol which was prepared essentially according to the above paragraph was then dealkylated by treating 21.6 grams of this material in the presence of 13.5 grams of a dealkylation catalyst comprising aluminum chloride and 45 grams of toluene. The aluminum chloride catalyst was present in about a 10% aqueous molar excess based on the 5-t-butyl-2-fluorophenol. The reaction was effected at a temperature in the range of from about 20° to 60° C. for a period of about 16 hours. At the end of this time, heating was discontinued and the product was recovered from the mixture by treating with water from which the o-fluorophenol was extracted with toluene after which the mixture was subjected to fractional distillation under reduced pressure and the desired product comprising 2-fluorophenol was recovered. Analysis of the product determined that there had been an 85% conversion of the alkylated fluorophenol with an 80% selectivity to 2-fluorophenol.

EXAMPLE II

In this example 5-t-butyl-2-fluorophenol which was prepared according to the method set forth in Example I above was treated in the presence of a 75/25 silica-alumina catalyst in the presence of toluene for a period of about 12.5 hours at a temperature of 280° C. Analysis of the reaction product after recovery from the autoclave determined that there had been a 94% conversion of the 5-t-butyl-2-fluorophenol with about 57% selectivity to 2-fluorophenol.

EXAMPLE III

In this example, fluorobenzene may be alkylated with sec-amylchloride by treating said fluorobenzene with the chloride in the presence of an aluminum chloride catalyst, the reaction being effected at subambient temperatures ranging from 0° to 5° C. The alkylation may be effected by slowly adding the sec-amylchloride to the fluorobenzene in a nitromethane solvent for a period of about 3–4 hours. Upon completion of the reaction period water may be added to hydrolyze the aluminum chloride catalyst while maintaining the temperature below about 10° C. The reaction contents are then separated in a separatory funnel following which the organic layer may be washed with water and dried. Thereafter the organic layer may be subjected to fractional distillation under reduced pressure to separate and recover the desired 4-sec-amylfluorobenzene. The thus formed 4-sec-amylfluorobenzene may then be brominated by treatment with bromine in the presence of an iodine catalyst, said bromine being added incrementally at a temperature of about 50° C. Upon completion of the desired residence time sodium thiosulfate may be added to effect the removal of the iodine and unreacted bromine from the organic reaction phase. Thereafter the organic phase may be washed with water and dried over anhydrous sodium sulfate. The product mixture may then be fractionated under reduced pressure and the desired product comprising 4-sec-amyl-2-bromo-fluorobenzene may be recovered. This product may then be hydrolyzed by treatment with water in the presence of potassium fluoride and cuprous oxide as a catalyst system plus sulfolane or N-methylpyrrolidone as a co-solvent, the hydrolysis being effected at an elevated temperature of about 250° C. and an elevated pressure of 550 psi. After completion of about an 8 hour residence time the autoclave and contents thereof may be allowed to return to room temperature and the excess pressure discharged. Thereafter the product may be subjected to fractional distillation to recover the 5-sec-amyl-2-fluorophenol.

The 5-sec-amyl-2-fluorophenol which may be prepared according to the above paragraph may then be dealkylated by treatment with an excess of ferric chloride in the presence of toluene as an acceptor for the liberated sec-amyl group. The desired product comprising 2-fluorophenol may be recovered by fractional distillation from the reaction mixture.

We claim as our invention:
1. A process for the preparation of 2-fluorophenol by dealkylation of 5-t-butyl-2-fluorophenol, which comprises contacting said 5-t-butyl-2-fluorophenol in admixture with an olefin acceptor comprising toluene or xylene with an acid acting catalyst selected from the group consisting of Friedel-Crafts metal halides, protonic acids, acid clays, alumina, and silica-alumina at a temperature of from about ambient to about 300° C. and a pressure of from about atmospheric to about 100 atmospheres, a time period of from about 0.5 to about 30 hours and a molar ratio of from about 1.1:1 to about 1.5:1 moles of catalyst per mole of phenol, and recovering the resultant 2-fluorophenol.

2. The process as set forth in claim 1 in which said acid acting catalyst is a Friedel-Crafts metal halide.

3. The process as set forth in claim 2 in which said Friedel-Crafts metal halide is aluminum chloride.

4. The process as set forth in claim 2 in which said Friedel-Crafts metal halide is ferric chloride.

5. The process as set forth in claim 1 in which said acid acting catalyst is p-toluenesulfonic acid.

6. The process as set forth in claim 1 in which said olefin acceptor compound is toluene.

7. The process as set forth in claim 1 in which said acid acting catalyst is silica-alumina and said olefin acceptor is toluene.

* * * * *